United States Patent
Mangual-Soto

(10) Patent No.: US 12,369,835 B2
(45) Date of Patent: *Jul. 29, 2025

(54) SYSTEM AND METHOD FOR ELECTROPHYSIOLOGICAL MAPPING

(71) Applicant: ST. JUDE MEDICAL, CARDIOLOGY DIVISION, INC., St. Paul, MN (US)

(72) Inventor: Jan O Mangual-Soto, Rho (IT)

(73) Assignee: St. Jude Medical, Cardiology Division, Inc., St. Paul, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 17/717,749

(22) Filed: Apr. 11, 2022

(65) Prior Publication Data
US 2022/0287614 A1 Sep. 15, 2022

Related U.S. Application Data

(63) Continuation of application No. 16/623,206, filed as application No. PCT/US2018/034643 on May 25, 2018, now Pat. No. 11,298,066.
(Continued)

(51) Int. Cl.
*A61B 5/00* (2006.01)
*A61B 5/283* (2021.01)
(Continued)

(52) U.S. Cl.
CPC .............. *A61B 5/339* (2021.01); *A61B 5/283* (2021.01); *A61B 5/349* (2021.01); *A61B 5/7475* (2013.01)

(58) Field of Classification Search
CPC ......... A61B 5/339; A61B 5/283; A61B 5/349; A61B 5/7475; A61B 5/343; A61B 5/347–367; A61B 5/743
See application file for complete search history.

(56) References Cited

U.S. PATENT DOCUMENTS 5,431,689 A * 7/1995 Weinberg ............. A61N 1/3621
607/14
5,697,377 A 12/1997 Wittkampf
(Continued)

FOREIGN PATENT DOCUMENTS

EP 2258263 12/2010

OTHER PUBLICATIONS

Flavia Ravelli et al., "Computational mapping in atrial fibrillation: how the integration of signal-derived maps may guide the localization of critical sources," Eurospace, vol. 16, No. 5, May 1, 2014, pp. 714-723.

*Primary Examiner* — Scott M. Getzow
(74) *Attorney, Agent, or Firm* — Wiley Rein LLP

(57) ABSTRACT

An electrophysiology map of a portion of a patient's anatomy can be visualized using an electroanatomical mapping system. The system receives a plurality of electrophysiology data points (e.g., an electrophysiology map), which includes a plurality of electrophysiology signals. The system then creates a distribution (e.g., a histogram) for one or more characteristics of the plurality of electrophysiology signals (e.g., dominant cycle length, regular cycle length, peak-to-peak voltage, fractionation, conduction velocity, or the like). The system then analyzes the distribution to determine a display convention (e.g., a range and scale) for a graphical representation of the characteristic based on, for example, a best-fit shape of the distribution, a skew of the distribution, a range of the distribution, and/or a most dominant value of the distribution. The graphical representation can then be output according to the display convention.

20 Claims, 7 Drawing Sheets

Related U.S. Application Data

(60) Provisional application No. 62/529,714, filed on Jul. 7, 2017.

(51) Int. Cl.
*A61B 5/339* (2021.01)
*A61B 5/349* (2021.01)

(56) References Cited

U.S. PATENT DOCUMENTS

| | | |
|---|---|---|
| 5,983,126 A | 11/1999 | Wittkampf |
| 6,640,119 B1 | 10/2003 | Budd et al. |
| 6,728,562 B1 | 4/2004 | Budd et al. |
| 6,939,309 B1 | 9/2005 | Beatty et al. |
| 6,947,785 B1 | 9/2005 | Beatty et al. |
| 6,978,168 B2 | 12/2005 | Beatty et al. |
| 6,990,370 B1 | 1/2006 | Beatty et al. |
| 7,263,397 B2 | 8/2007 | Hauck et al. |
| 7,885,707 B2 | 2/2011 | Hauck |
| 2005/0187588 A1 | 8/2005 | Stahmann et al. |
| 2007/0197929 A1* | 8/2007 | Porath .................... A61B 5/349 600/509 |
| 2009/0124915 A1 | 5/2009 | MacAdam |
| 2012/0157864 A1* | 6/2012 | Thakur ................ A61B 5/0538 600/508 |
| 2015/0057507 A1 | 2/2015 | Koyrakh et al. |
| 2015/0313491 A1* | 11/2015 | Edwards ................ G16Z 99/00 600/509 |
| 2017/0079539 A1* | 3/2017 | Chauhan ................ A61B 5/339 |
| 2019/0142282 A1 | 5/2019 | De Morree |

* cited by examiner

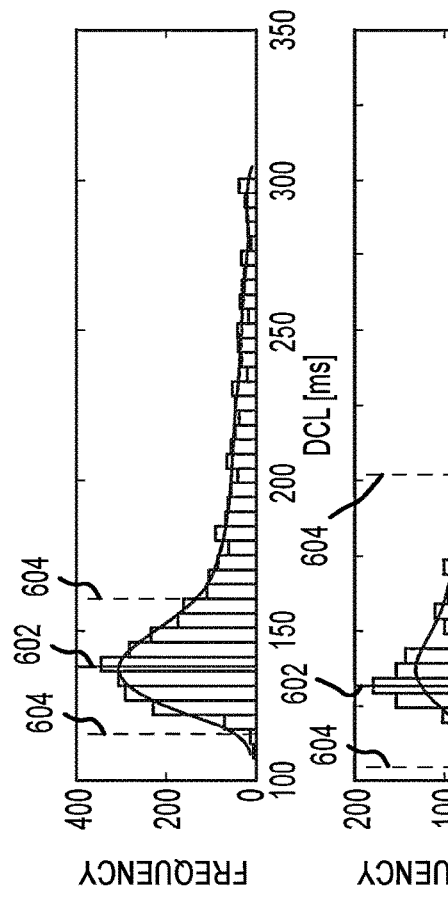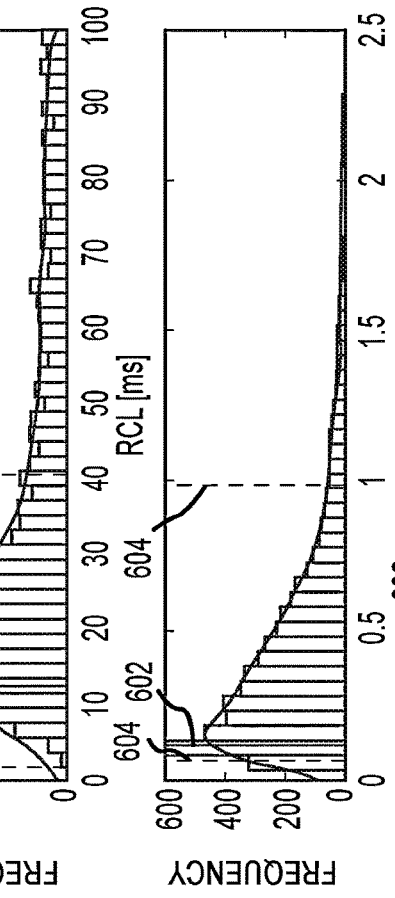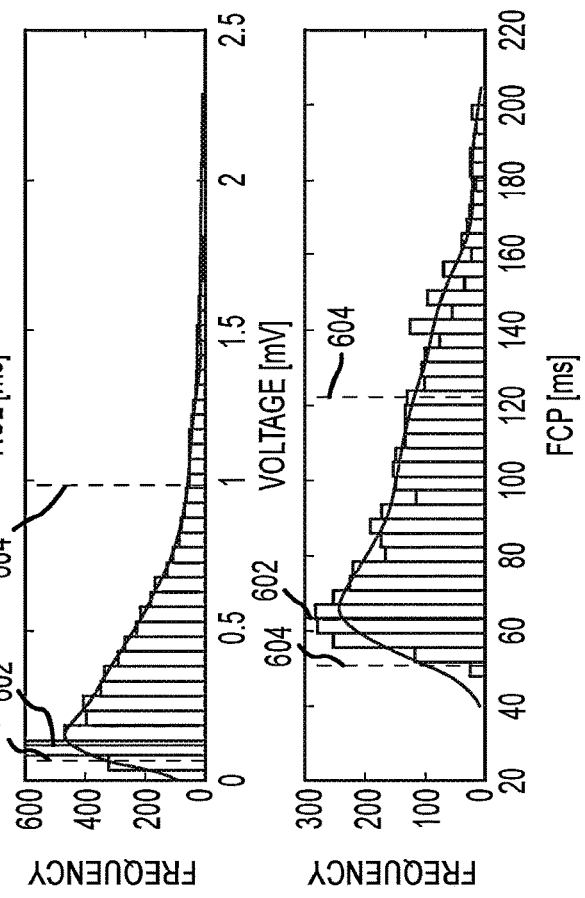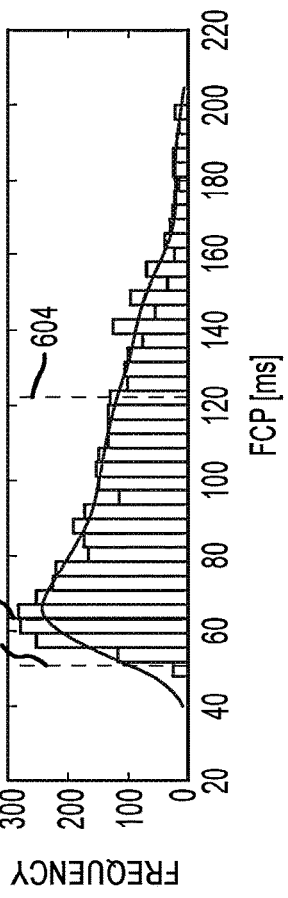

SYSTEM AND METHOD FOR ELECTROPHYSIOLOGICAL MAPPING

CROSS-REFERENCE TO RELATED APPLICATIONS

This application is a continuation of U.S. application Ser. No. 16/623,206 filed 16 Dec. 2019 ("the '206 application"), now U.S. Pat. No. 11,298,066, which is a national stage entry of international application no. PCT/US2018/034643 ("the '643 PCT"), which claims the benefit of U.S. provisional application No. 62/529,714, filed 7 Jul. 2017 ("the '714 provisional"). The '206 application, the '643 PCT, and the '714 provisional are hereby incorporated by reference as though fully set forth herein.

BACKGROUND

The present disclosure relates generally to cardiac therapeutic procedures, such as cardiac ablation. In particular, the present disclosure relates to systems, apparatuses, and methods for generating electrophysiological maps.

Electrophysiological mapping, and more particularly electrocardiographic mapping, is a part of numerous cardiac and diagnostic and therapeutic procedures. As the complexity of such procedures increases, however, the electrophysiology maps utilized must increase in quality, in density, and in the rapidity and ease with which they can be generated.

Arrhythmias can often be the result of several characteristics of diseased tissue, such as low voltage/scar tissue, substrate with fast/regular erratic activation, or regions that cause fragmentation of the electrical propagation. Accordingly, extant electroanatomical mapping systems and related devices (e.g., electrophysiology catheters) offer physicians various methods for tissue characterization.

Given the volume of electrophysiology data collected in an electrophysiology study (e.g., 1000+ electrophysiology data points in a single cardiac chamber) and the number of electrophysiological characteristics that can be analyzed and/or displayed (e.g., voltage, activation time, cycle length, conduction velocity, and so on), it can be challenging to generate a clear and easily interpreted visualization of the electrophysiological activity.

BRIEF SUMMARY

Disclosed herein is a method of visualizing an electrophysiology map of a portion of a patient's anatomy using an electroanatomical mapping system. The method includes: the electroanatomical mapping system receiving a plurality of electrophysiology data points, the plurality of electrophysiology data points including a plurality of electrophysiology signals; the electroanatomical mapping system analyzing the plurality of electrophysiology signals to determine a distribution for at least one characteristic of the plurality of electrophysiology signals; and the electroanatomical mapping outputting a graphical representation of the at least one characteristic of the plurality of electrophysiology signals, wherein a display convention for the graphical representation is determined according to the distribution for the at least one characteristic of the plurality of electrophysiology signals.

The step of analyzing the plurality of electrophysiological signals to determine a distribution for at least one characteristic of the plurality of electrophysiology signals can include analyzing the plurality of electrophysiological signals to determine any of: a distribution for dominant cycle lengths of the plurality of electrophysiology signals; a distribution for regular cycle lengths of the plurality of electrophysiology signals; a distribution for peak-to-peak voltages of the plurality of electrophysiology signals; a distribution for fractionated potentials of the plurality of electrophysiology signals; and/or a distribution for conduction velocities of the plurality of electrophysiology signals.

The step of analyzing the plurality of electrophysiological signals to determine a distribution for at least one characteristic of the plurality of electrophysiology signals can also include determining one or more of: a best-fit shape of the distribution; a skew of the distribution; a range of the distribution; and a most dominant value of the distribution.

It is contemplated that the step of analyzing the plurality of electrophysiological signals to determine a distribution for at least one characteristic of the plurality of electrophysiology signals includes generating a histogram for the at least one characteristic of the plurality of electrophysiology signals.

According to aspects of the disclosure, a range for the display convention and a scale for the display convention are set according to at least one of a best-fit shape of the distribution, a skew of the distribution, a range of the distribution, and a most dominant value of the distribution.

Also disclosed herein is a method of visualizing an electrophysiology map of a portion of a patient's anatomy using an electroanatomical mapping system, including the steps of: the electroanatomical mapping system receiving a plurality of electrophysiology data points, the plurality of electrophysiology data points including a plurality of electrophysiology signals; the electroanatomical mapping system creating a histogram of values of a characteristic of the plurality of electrophysiology signals; the electroanatomical mapping system analyzing the histogram of values to determine a display convention for a graphical representation of the characteristic; and the electroanatomical mapping system outputting the graphical representation of the characteristic according to the display convention.

In embodiments of the disclosure, a range of the display convention can be determined according to one or more of a best-fit shape of the histogram, a skew of the histogram, a range of the histogram, and a most dominant value of the histogram. For example, the range of the display convention can be defined as a range about a most dominant value of the histogram. For example, according to aspects of the disclosure, the range of the display convention can be defined as the most dominant value of the histogram plus-or-minus 45% of a range of the histogram.

According to additional aspects of the disclosure, a scale of the display convention can be determined according to one or more of a best-fit shape of the histogram, a skew of the histogram, a range of the histogram, and a most dominant value of the histogram.

In embodiments, the characteristic includes dominant cycle length, and the step of creating a histogram of values includes binning values of dominant cycle length into bins of about 5 ms width ranging from about 100 ms to about 300 ms.

In other embodiments, the characteristic includes regular cycle length, and the step of creating a histogram of values includes binning values of regular cycle length into bins of about 2 ms width ranging from about 0 ms to about 100 ms.

In still other embodiments, the characteristic includes peak-to-peak voltage, and the step of creating a histogram of values includes binning values of peak-to-peak voltage into bins of about 0.05 mV width ranging from about 0 mV to about 2.5 mV.

In further embodiments, the characteristic includes fractionation, and the step of creating a histogram of values includes binning values of fractionation into bins of about 5 ms width ranging from about 50 ms to about 200 ms.

In yet further embodiments, the characteristic includes conduction velocity, and the step of creating a histogram of values includes binning values of conduction velocity into bins of about 0.05 mm/s width ranging from about 0 mm/s to about 2 mm/s.

The instant disclosure also provides a system for visualizing an electrophysiology map of a portion of a patient's anatomy, including a visualization processor configured to: receive as input a plurality of electrophysiology data points, the plurality of electrophysiology data points including a plurality of electrophysiology signals; create a histogram of values of a characteristic of the plurality of electrophysiology signals; analyze the histogram of values to determine a display convention for a graphical representation of the characteristic; and output the graphical representation of the characteristic according to the display convention. For instance, a range of the display convention and a scale of the display convention can be determined according to one or more of a best-fit shape of the histogram, a skew of the histogram, a range of the histogram, and a most dominant value of the histogram.

The foregoing and other aspects, features, details, utilities, and advantages of the present invention will be apparent from reading the following description and claims, and from reviewing the accompanying drawings.

BRIEF DESCRIPTION OF THE DRAWINGS

FIGS. 6A, 6B, 6C, and 6D are distributions corresponding to FIGS. 5A, 5B, 5C, and 5D, respectively.

While multiple embodiments are disclosed, still other embodiments of the present disclosure will become apparent to those skilled in the art from the following detailed description, which shows and describes illustrative embodiments. Accordingly, the drawings and detailed description are to be regarded as illustrative in nature and not restrictive.

DETAILED DESCRIPTION

The instant disclosure provides systems, apparatuses, and methods for generating electrophysiology maps (e.g., electrocardiographic maps). For purposes of illustration, aspects of the disclosure will be described in the context of a cardiac electrophysiology procedure. It should be understood, however, that the teachings herein can be applied to good advantage in other contexts.

Figure 1:
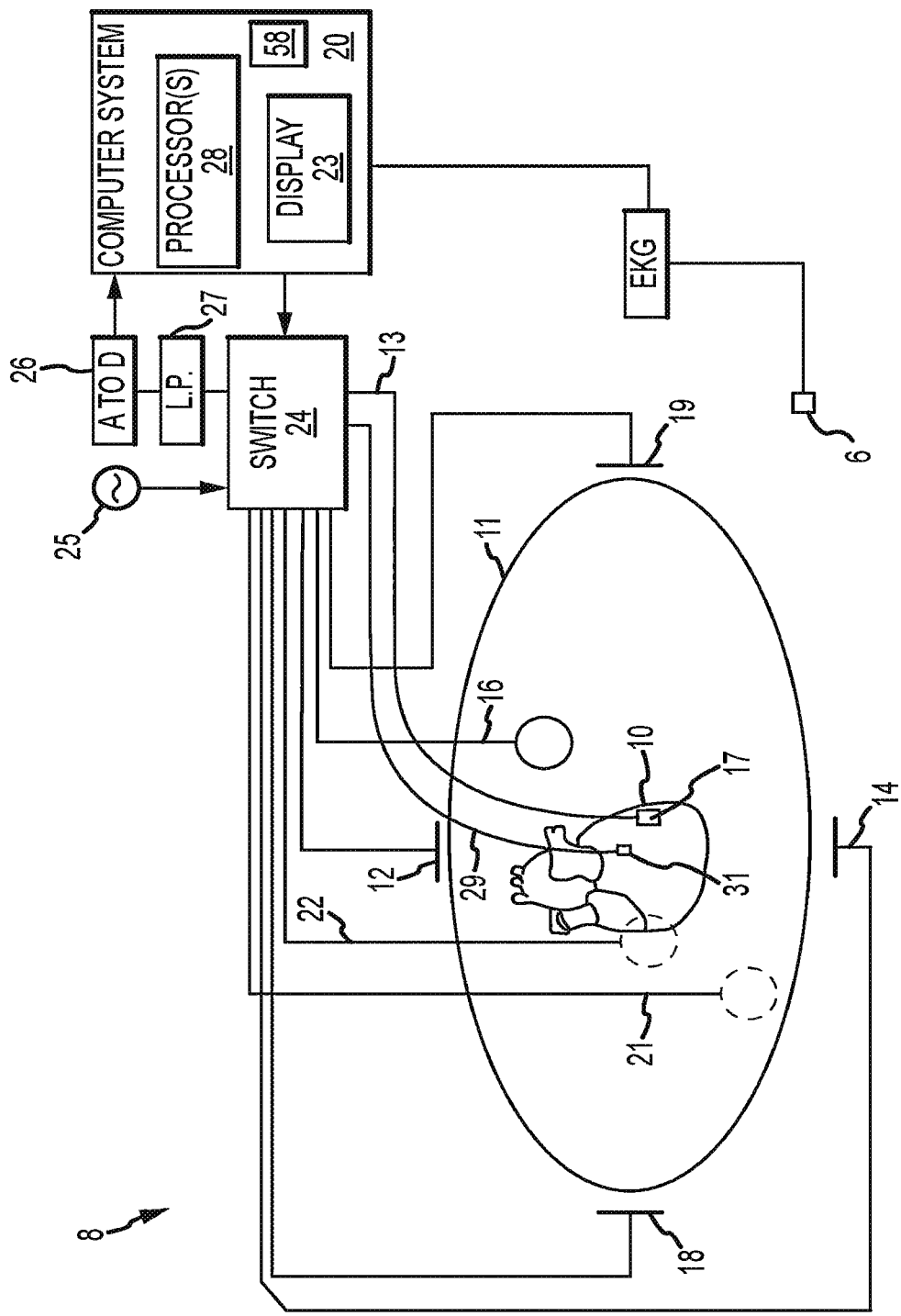
FIG. 1 is a schematic diagram of an exemplary electroanatomical mapping system.

FIG. 1 shows a schematic diagram of an exemplary electroanatomical mapping system 8 for conducting cardiac electrophysiology studies by navigating a cardiac catheter and measuring electrical activity occurring in a heart 10 of a patient 11 and three-dimensionally mapping the electrical activity and/or information related to or representative of the electrical activity so measured. System 8 can be used, for example, to create an anatomical model of the patient's heart 10 using one or more electrodes. System 8 can also be used to measure electrophysiology data at a plurality of points along a cardiac surface and store the measured data in association with location information for each measurement point at which the electrophysiology data was measured, for example to create a diagnostic data map of the patient's heart 10.

As one of ordinary skill in the art will recognize, and as will be further described below, system 8 determines the location, and in some aspects the orientation, of objects, typically within a three-dimensional space, and expresses those locations as position information determined relative to at least one reference.

For simplicity of illustration, the patient 11 is depicted schematically as an oval. In the embodiment shown in FIG. 1, three sets of surface electrodes (e.g., patch electrodes) are shown applied to a surface of the patient 11, defining three generally orthogonal axes, referred to herein as an x-axis, a y-axis, and a z-axis. In other embodiments the electrodes could be positioned in other arrangements, for example multiple electrodes on a particular body surface. As a further alternative, the electrodes do not need to be on the body surface, but could be positioned internally to the body.

In FIG. 1, the x-axis surface electrodes 12, 14 are applied to the patient along a first axis, such as on the lateral sides of the thorax region of the patient (e.g., applied to the patient's skin underneath each arm) and may be referred to as the Left and Right electrodes. The y-axis electrodes 18, 19 are applied to the patient along a second axis generally orthogonal to the x-axis, such as along the inner thigh and neck regions of the patient, and may be referred to as the Left Leg and Neck electrodes. The z-axis electrodes 16, 22 are applied along a third axis generally orthogonal to both the x-axis and the y-axis, such as along the sternum and spine of the patient in the thorax region, and may be referred to as the Chest and Back electrodes. The heart 10 lies between these pairs of surface electrodes 12/14, 18/19, and 16/22.

An additional surface reference electrode (e.g., a "belly patch") 21 provides a reference and/or ground electrode for the system 8. The belly patch electrode 21 may be an alternative to a fixed intra-cardiac electrode 31, described in further detail below. It should also be appreciated that, in addition, the patient 11 may have most or all of the conventional electrocardiogram ("ECG" or "EKG") system leads in place. In certain embodiments, for example, a standard set of 12 ECG leads may be utilized for sensing electrocardiograms on the patient's heart 10. This ECG information is available to the system 8 (e.g., it can be provided as input to computer system 20). Insofar as ECG leads are well understood, and for the sake of clarity in the figures, only a single lead 6 and its connection to computer 20 is illustrated in FIG. 1.

A representative catheter 13 having at least one electrode 17 is also shown. This representative catheter electrode 17 is referred to as the "roving electrode," "moving electrode," or "measurement electrode" throughout the specification. Typically, multiple electrodes 17 on catheter 13, or on multiple such catheters, will be used. In one embodiment, for example, the system 8 may comprise sixty-four electrodes on twelve catheters disposed within the heart and/or vasculature of the patient. Of course, this embodiment is merely exemplary, and any number of electrodes and catheters may be used.

Figure 2:
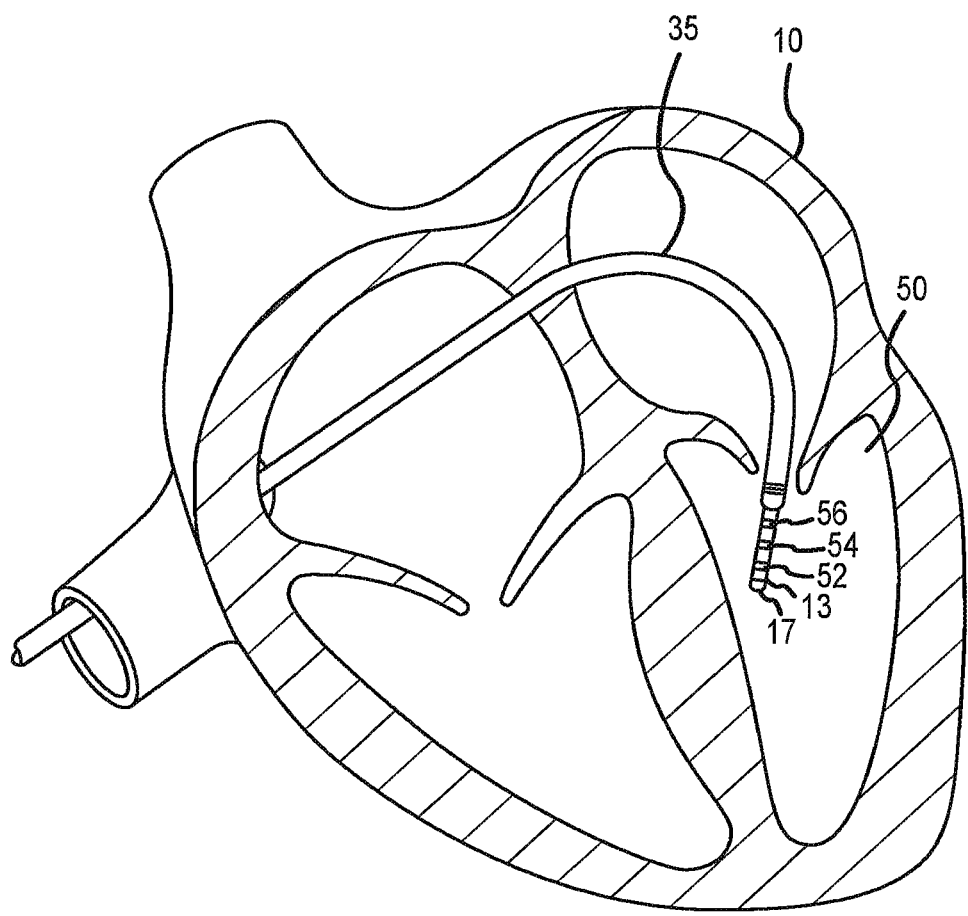
FIG. 2 depicts an exemplary catheter that can be used in connection with aspects of the instant disclosure.

Likewise, it should be understood that catheter 13 (or multiple such catheters) are typically introduced into the heart and/or vasculature of the patient via one or more introducers and using familiar procedures. For purposes of this disclosure, a segment of an exemplary multi-electrode catheter 13 is shown in FIG. 2. In FIG. 2, catheter 13 extends into the left ventricle 50 of the patient's heart 10 through a transseptal sheath 35. The use of a transseptal approach to the left ventricle is well known and will be familiar to those of ordinary skill in the art, and need not be further described herein. Of course, catheter 13 can also be introduced into the heart 10 in any other suitable manner.

Catheter 13 includes electrode 17 on its distal tip, as well as a plurality of additional measurement electrodes 52, 54, 56 spaced along its length in the illustrated embodiment. Typically, the spacing between adjacent electrodes will be known, though it should be understood that the electrodes may not be evenly spaced along catheter 13 or of equal size to each other. Since each of these electrodes 17, 52, 54, 56 lies within the patient, location data may be collected simultaneously for each of the electrodes by system 8.

Similarly, each of electrodes 17, 52, 54, and 56 can be used to gather electrophysiological data from the cardiac surface. The ordinarily skilled artisan will be familiar with various modalities for the acquisition and processing of electrophysiology data points (including, for example, both contact and non-contact electrophysiological mapping), such that further discussion thereof is not necessary to the understanding of the techniques disclosed herein. Likewise, various techniques familiar in the art can be used to generate a graphical representation from the plurality of electrophysiology data points. Insofar as the ordinarily skilled artisan will appreciate how to create electrophysiology maps from electrophysiology data points, the aspects thereof will only be described herein to the extent necessary to understand the instant disclosure.

Returning now to FIG. 1, in some embodiments, an optional fixed reference electrode 31 (e.g., attached to a wall of the heart 10) is shown on a second catheter 29. For calibration purposes, this electrode 31 may be stationary (e.g., attached to or near the wall of the heart) or disposed in a fixed spatial relationship with the roving electrodes (e.g., electrodes 17), and thus may be referred to as a "navigational reference" or "local reference." The fixed reference electrode 31 may be used in addition or alternatively to the surface reference electrode 21 described above. In many instances, a coronary sinus electrode or other fixed electrode in the heart 10 can be used as a reference for measuring voltages and displacements; that is, as described below, fixed reference electrode 31 may define the origin of a coordinate system.

Each surface electrode is coupled to a multiplex switch 24, and the pairs of surface electrodes are selected by software running on a computer 20, which couples the surface electrodes to a signal generator 25. Alternately, switch 24 may be eliminated and multiple (e.g., three) instances of signal generator 25 may be provided, one for each measurement axis (that is, each surface electrode pairing).

The computer 20 may comprise, for example, a conventional general-purpose computer, a special-purpose computer, a distributed computer, or any other type of computer.

The computer 20 may comprise one or more processors 28, such as a single central processing unit ("CPU"), or a plurality of processing units, commonly referred to as a parallel processing environment, which may execute instructions to practice the various aspects described herein.

Generally, three nominally orthogonal electric fields are generated by a series of driven and sensed electric dipoles (e.g., surface electrode pairs 12/14, 18/19, and 16/22) in order to realize catheter navigation in a biological conductor. Alternatively, these orthogonal fields can be decomposed and any pairs of surface electrodes can be driven as dipoles to provide effective electrode triangulation. Likewise, the electrodes 12, 14, 18, 19, 16, and 22 (or any number of electrodes) could be positioned in any other effective arrangement for driving a current to or sensing a current from an electrode in the heart. For example, multiple electrodes could be placed on the back, sides, and/or belly of patient 11. Additionally, such non-orthogonal methodologies add to the flexibility of the system. For any desired axis, the potentials measured across the roving electrodes resulting from a predetermined set of drive (source-sink) configurations may be combined algebraically to yield the same effective potential as would be obtained by simply driving a uniform current along the orthogonal axes.

Thus, any two of the surface electrodes 12, 14, 16, 18, 19, 22 may be selected as a dipole source and drain with respect to a ground reference, such as belly patch 21, while the unexcited electrodes measure voltage with respect to the ground reference. The roving electrodes 17 placed in the heart 10 are exposed to the field from a current pulse and are measured with respect to ground, such as belly patch 21. In practice the catheters within the heart 10 may contain more or fewer electrodes than the sixteen shown, and each electrode potential may be measured. As previously noted, at least one electrode may be fixed to the interior surface of the heart to form a fixed reference electrode 31, which is also measured with respect to ground, such as belly patch 21, and which may be defined as the origin of the coordinate system relative to which system 8 measures positions. Data sets from each of the surface electrodes, the internal electrodes, and the virtual electrodes may all be used to determine the location of the roving electrodes 17 within heart 10.

The measured voltages may be used by system 8 to determine the location in three-dimensional space of the electrodes inside the heart, such as roving electrodes 17 relative to a reference location, such as reference electrode 31. That is, the voltages measured at reference electrode 31 may be used to define the origin of a coordinate system, while the voltages measured at roving electrodes 17 may be used to express the location of roving electrodes 17 relative to the origin. In some embodiments, the coordinate system is a three-dimensional (x, y, z) Cartesian coordinate system, although other coordinate systems, such as polar, spherical, and cylindrical coordinate systems, are contemplated.

As should be clear from the foregoing discussion, the data used to determine the location of the electrode(s) within the heart is measured while the surface electrode pairs impress an electric field on the heart. The electrode data may also be used to create a respiration compensation value used to improve the raw location data for the electrode locations as described, for example, in U.S. Pat. No. 7,263,397, which is hereby incorporated herein by reference in its entirety. The electrode data may also be used to compensate for changes in the impedance of the body of the patient as described, for example, in U.S. Pat. No. 7,885,707, which is also incorporated herein by reference in its entirety.

Therefore, in one representative embodiment, system 8 first selects a set of surface electrodes and then drives them with current pulses. While the current pulses are being delivered, electrical activity, such as the voltages measured with at least one of the remaining surface electrodes and in vivo electrodes, is measured and stored. Compensation for artifacts, such as respiration and/or impedance shifting, may be performed as indicated above.

In some embodiments, system 8 is the EnSite™ Velocity™ or EnSite Precision™ cardiac mapping and visualization system of Abbott Laboratories. Other localization systems, however, may be used in connection with the present teachings, including for example the RHYTHMIA HDX™ mapping system of Boston Scientific Corporation, the CARTO navigation and location system of Biosense Webster, Inc., the AURORA® system of Northern Digital Inc., Sterotaxis' NIOBE® Magnetic Navigation System, as well as MediGuide™ Technology from Abbott Laboratories.

The localization and mapping systems described in the following patents (all of which are hereby incorporated by reference in their entireties) can also be used with the present invention: U.S. Pat. Nos. 6,990,370; 6,978,168; 6,947,785; 6,939,309; 6,728,562; 6,640,119; 5,983,126; and 5,697,377.

Aspects of the disclosure relate to the visualization (e.g., graphical representation) of electrophysiology maps, such as on display 23. System 8 can therefore also include a visualization module 58 that can be used to generate graphical representations of electrophysiology maps.

Those of ordinary skill in the art will appreciate that electrophysiology maps include a plurality of electrophysiology data points, and that each electrophysiology data point in turn includes both measured electrophysiology data (e.g., an electrophysiological signal, such as a cardiac electrogram ("EGM")) and location data (e.g., information regarding the location of catheter 13 and/or electrodes 17, 52, 54, 56 thereon), allowing the measured electrophysiology information to be associated with a particular location in space (that is, allowing the measured electrophysiology information to be interpreted as indicative of electrical activity at a point on the patient's heart). Those of ordinary skill in the art will also be familiar with various aspects of the collection of electrophysiology data points and the creation of electrophysiology maps therefrom. By way of example only, however, United States patent application publication no. 2015/0057507, which is hereby incorporated by reference as though fully set forth herein, describes various methods and systems for the collection of electrophysiology data points and the creation of electrophysiology maps to which the teachings of the instant disclosure can be applied.

Figure 3:
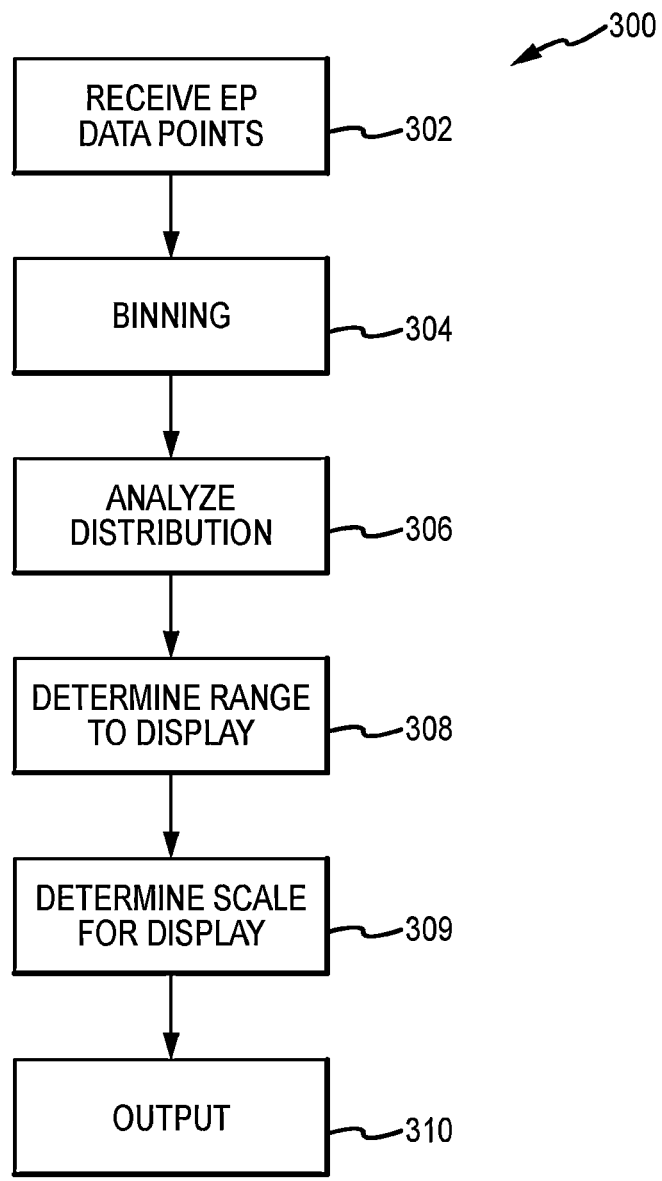
FIG. 3 is a flowchart of representative steps that can be followed according to exemplary embodiments disclosed herein.

One exemplary method of visualizing electrophysiology maps according to the present teachings will be explained with reference to the flowchart 300 of representative steps presented as FIG. 3. In some embodiments, for example, flowchart 300 may represent several exemplary steps that can be carried out by electroanatomical mapping system 8 of FIG. 1 (e.g., by processor 28 and/or visualization module 58). It should be understood that the representative steps described below can be either hardware- or software-implemented. For the sake of explanation, the term "signal processor" is used herein to describe both hardware- and software-based implementations of the teachings herein.

In block 302, system 8 receives a plurality of electrophysiology data points. As those of ordinary skill in the art will appreciate, the plurality of electrophysiology data points includes a plurality of electrophysiological signals. In turn, each of the electrophysiological signals possesses a plurality of characteristics, such as a dominant cycle length, a regular cycle length, a peak-to-peak voltage, a fractionation, a conduction velocity, and so forth.

System 8 analyzes the plurality of electrophysiology signals received in block 302 to determine a distribution of one or more characteristics of the signals. For example, a binning operation can be carried out in block 304, thereby generating a histogram for the one or more characteristics of the signals.

Different bin widths and ranges are contemplated for different signal characteristics. For example:
Dominant cycle length can be binned into bins of about 5 ms width, ranging from about 100 ms to about 300 ms.
Regular cycle length can be binned into bins of about 2 ms width, ranging from about 0 ms to about 100 ms.
Peak-to-peak voltage can be binned into bins of about 0.05 mV width, ranging from about 0 mV to about 2.5 mV.
Fractionated potentials can be binned into bins of about 5 ms width, ranging from about 50 ms to about 200 ms.
Conduction velocity can be binned into bins of about 0.05 mm/s width, ranging from about 0 mm/s to about 2 mm/s.

Figure 4:
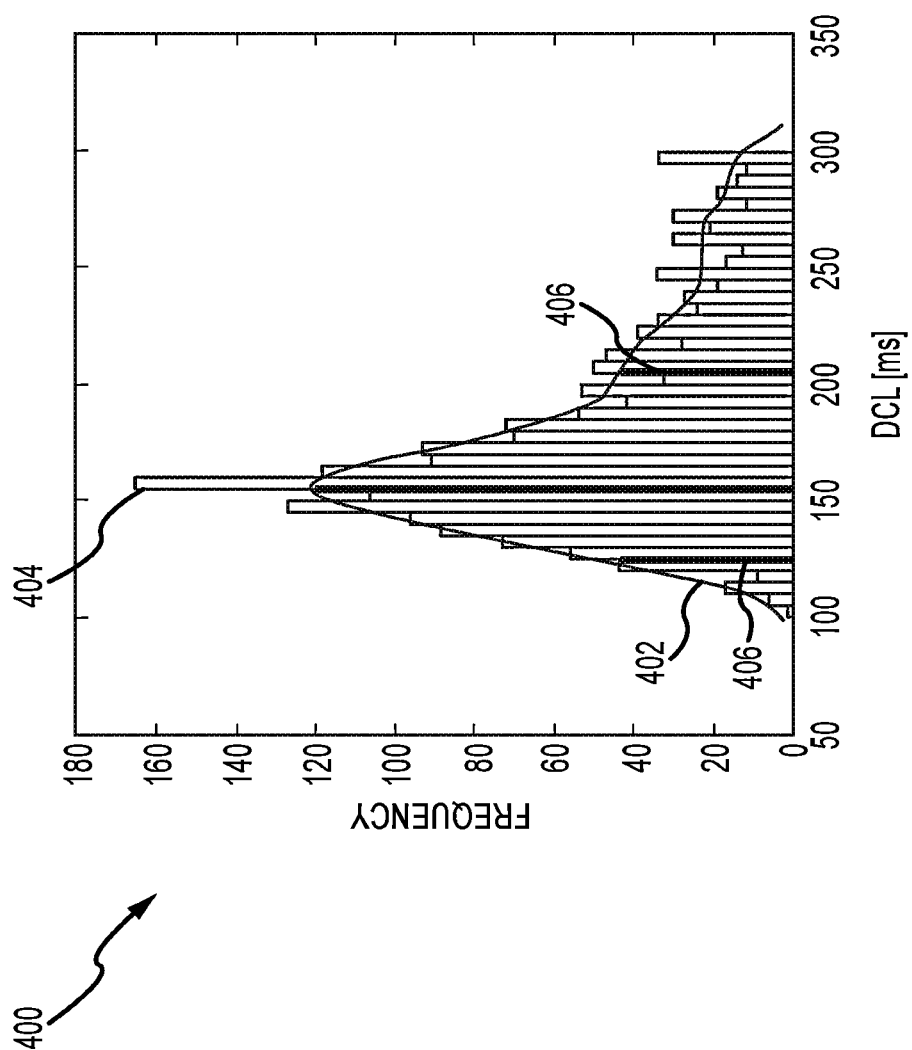
FIG. 4 is a representative distribution of dominant cycle lengths.
Figure 5A:
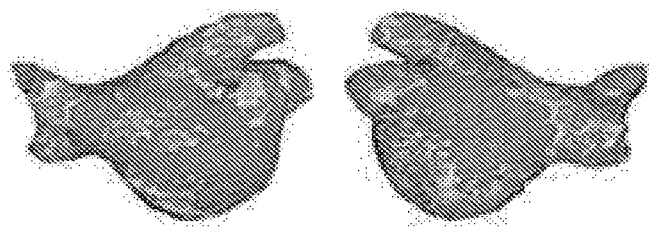
FIGS. 5A, 5B, 5C, and 5D are raw electrophysiology maps depicting, respectively, dominant cycle length, regular cycle length, peak-to-peak voltage, and fractionation.
Figure 5B:
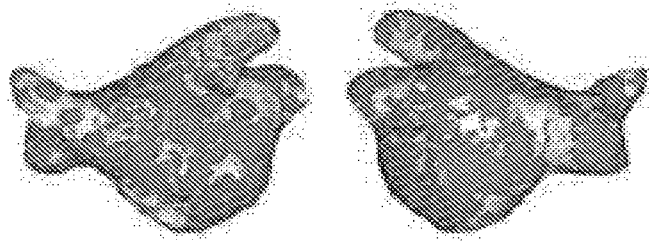
Figure 5C:
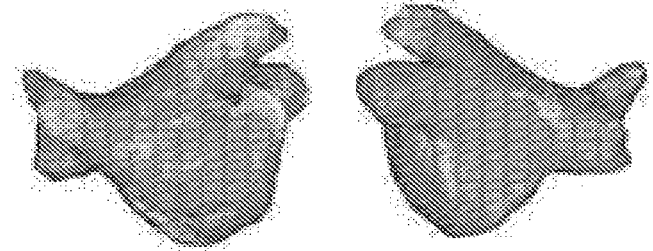
Figure 5D:
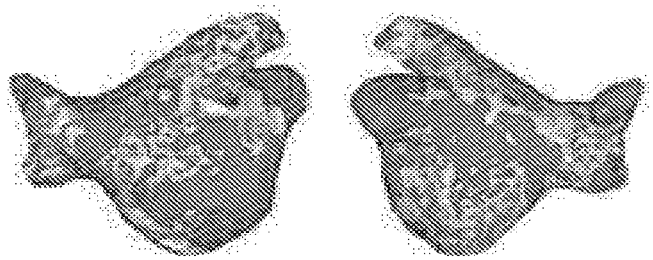
Figure 7A:
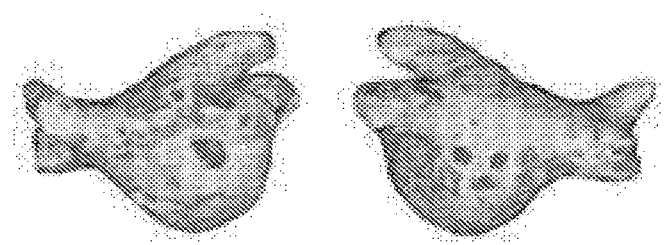
FIGS. 7A, 7B, 7C, and 7D are electrophysiology maps depicting, respectively, dominant cycle length, regular cycle length, peak-to-peak voltage, and fractionation, with display conventions determined using the distributions of FIGS. 6A, 6B, 6C, and 6D as disclosed herein.
Figure 7B:
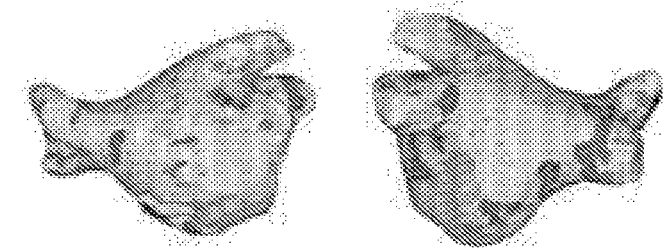
Figure 7C:
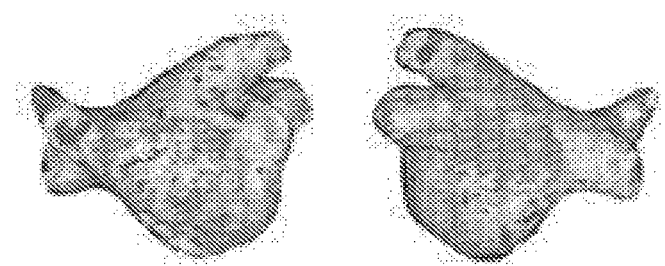
Figure 7D:
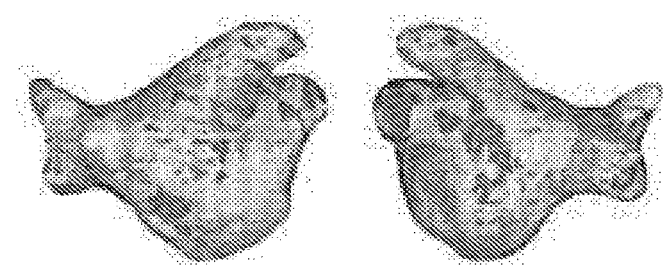

FIG. 4 is a representative histogram 400 for dominant cycle length (e.g., bins of 5 ms width, ranging from 100 ms to 300 ms). The present teachings will be explained with further reference to histogram 400 of dominant cycle length, but those of ordinary skill in the art will appreciate how to apply the teachings described herein to any other characteristics of electrophysiology signals, including, without limitation, those mentioned above.

In block 306, the binned data can be analyzed to determine a best-fit shape of the distribution (e.g., normal distribution; log-normal distribution; or the like), a skew of the distribution, a range of the distribution, and a most dominant value of the distribution. For instance, in FIG. 4, curve 402 depicts the best-fit shape of the distribution; the skew of the distribution is positive, the range of the distribution is from 100 ms to 300 ms, and the most dominant value of the distribution (e.g., the highest peak 404) is 150-155 ms.

Electroanatomical mapping system 8 determines a display convention, such as a color spectrum, a grayscale, a pattern density range, or the like, for a graphical representation of a dominant cycle length map in blocks 308 and 309. According to embodiments disclosed herein, the display convention is determined based on the distribution 400 of dominant cycle lengths.

For example, a range of values to display (e.g., color-high and color-low cutoffs values) can be selected based on distribution 400 in block 308. In aspects of the disclosure, the low-end cutoff can be the dominant value/peak 404 −45%, and the high-end cutoff can be the dominant value/peak 404 +45%, as shown by boundary marks 406 in FIG. 4.

As another example, the scale of the display convention—that is, whether the color spectrum, grayscale, pattern density range, or the like is linear, logarithmic, non-linear, etc. between the low- and high-end cutoff values—can also be selected in block 309 based on the best-fit shape 402 of distribution 400.

In some aspects of the disclosure, the display convention is set automatically prior to outputting the graphical representation of the dominant cycle length map in block 310. Alternatively, electroanatomical mapping system 8 can make display convention recommendations to a practitioner, but the practitioner can retain the ability to alter these recommendations (e.g., selecting different upper and/or lower bounds; selecting a different scale) prior to outputting the graphical representation of the dominant cycle length map in block 310.

Aspects of the instant disclosure are illustrated in FIGS. 5A-5C, 6A-6C, 7A-7C, and 8A-8C. FIGS. 5A, 5B, 5C, and 5D respectively depict a dominant cycle length map, a regular cycle length map, a peak-to-peak voltage map, and a fractionation map without application of the teachings herein (e.g., with all collected electrophysiology data points shown).

FIGS. 6A, 6B, 6C, and 6D respectively depict the distributions for dominant cycle length, regular cycle length, peak-to-peak voltage, and fractionation depicted in FIGS. 5A-5D. FIGS. 6A, 6B, 6C, and 6D also depict dominant values/peaks 602 and boundary marks 604, the latter of which can represent the low- and high-end cutoff values. As described above, according to aspects of the disclosure, boundary marks 604 can be set at the dominant value/peak 602 plus-or-minus 45%; this is shown in FIG. 6A.

In other embodiments of the disclosure, boundary marks 604 can be positioned around the dominant value/peak 602 by the user based on a visual inspection of the distribution. This is illustrated, for example, in FIGS. 6B, 6C, and 6D.

Finally, FIGS. 7A, 7B, 7C, and 7D depict maps of dominant cycle length, regular cycle length, peak-to-peak voltage, and fractionation with display conventions determined according to the teachings herein.

Application of the teachings herein advantageously allow electrophysiology maps to be displayed with increased granularity and clarity. This, in turn, facilitates rapid assimilation and understanding of even voluminous collected electrophysiology data by practitioners.

Although several embodiments have been described above with a certain degree of particularity, those skilled in the art could make numerous alterations to the disclosed embodiments without departing from the spirit or scope of this invention.

For example, the teachings herein can be applied in real time (e.g., during an electrophysiology study) or during post-processing (e.g., to electrophysiology data points collected during an electrophysiology study performed at an earlier time).

As another example, those of ordinary skill in the art will appreciate that the values and ranges (e.g., bin widths and ranges) disclosed herein are merely exemplary and can be altered, for example by a practitioner during an electrophysiology study, without departing from the scope of the present disclosure.

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A method of visualizing electrophysiological activity of a portion of a patient's anatomy using an electroanatomical mapping system, the electroanatomical mapping system including a display, the method comprising the electroanatomical mapping system:
   receiving a plurality of electrophysiology data points measured by an electrophysiology catheter, the plurality of electrophysiology data points comprising a plurality of electrophysiology signals;
   creating a frequency curve of a distribution of values of a characteristic of the plurality of electrophysiology signals;
   outputting a graphical representation of the frequency curve; and
   outputting a graphical representation of the characteristic of the plurality of electrophysiology signals on a three-dimensional representation of the portion of the patient's anatomy, wherein a range of a display convention for the graphical representation of the characteristic of the plurality of electrophysiology signals is determined according to the frequency curve and centered at a most dominant value of the frequency curve.

2. The method according to claim 1, wherein the characteristic comprises dominant cycle length.

3. The method according to claim 1, wherein the characteristic comprises regular cycle length.

4. The method according to claim 1, wherein the characteristic comprises peak-to-peak voltage.

5. The method according to claim 1, wherein the characteristic comprises fractionation.

6. The method according to claim 1, wherein the characteristic comprises conduction velocity.

7. The method according to claim 1, wherein the frequency curve comprises a best fit curve to the distribution of values.

8. A method of visualizing electrical activity on a surface of a heart using an electroanatomical mapping system including a display, the method comprising the electroanatomical mapping system:
   receiving a plurality of electrograms measured by an electrophysiology catheter from the surface of the heart;
   analyzing the plurality of electrograms to determine a statistical distribution of a characteristic of the plurality of electrograms, wherein the characteristic is indicative of electrical activity on the surface of the heart;
   outputting a graphical representation of the statistical distribution of the characteristic of the plurality of electrograms; and
   outputting a graphical representation of the characteristic of the plurality of electrograms on a three-dimensional representation of the surface of the heart, wherein a range of a display convention for the graphical representation of the characteristic of the plurality of electrograms is determined according to the statistical distribution and centered at a most dominant value of the statistical distribution.

9. The method according to claim 8, wherein the characteristic comprises dominant cycle length.

10. The method according to claim 8, wherein the characteristic comprises regular cycle length.

11. The method according to claim 8, wherein the characteristic comprises peak-to-peak voltage.

12. The method according to claim 8, wherein the characteristic comprises fractionation.

13. The method according to claim 8, wherein the characteristic comprises conduction velocity.

14. The method according to claim 8, wherein outputting the graphical representation of the statistical distribution of the characteristic of the plurality of electrograms comprises outputting a best-fit curve to the statistical distribution of the characteristic of the plurality of electrograms.

15. The method according to claim 8, wherein outputting the graphical representation of the statistical distribution of the characteristic of the plurality of electrograms comprises outputting a histogram of the statistical distribution of the characteristic of the plurality of electrograms.

16. A system for visualizing electrical activity on a surface of a heart, comprising:
    an electrophysiology catheter;
    a display; and
    a visualization processor configured to:
        receive as input a plurality of electrograms from the surface of the heart, the electrograms measured by the electrophysiology catheter;
        analyze the plurality of electrograms to determine a statistical distribution of a characteristic of the plurality of electrograms, wherein the characteristic is indicative of electrical activity on the surface of the heart;
        output a graphical representation of the statistical distribution of the characteristic of the plurality of electrograms on the display; and
        output on the display a graphical representation of the characteristic of the plurality of electrograms on a three-dimensional representation of the surface of the heart, wherein a range of a display convention for the graphical representation of the characteristic of the plurality of electrograms is determined according to the statistical distribution and centered at a most dominant value of the statistical distribution.

17. The system according to claim 16, wherein the characteristic comprises cycle length.

18. The system according to claim 16, wherein the characteristic comprises conduction velocity.

19. The system according to claim 16, wherein the graphical representation comprises a best-fit curve to the statistical distribution of the characteristic of the plurality of electrograms.

20. The system according to claim 16, wherein the graphical representation comprises a histogram of the statistical distribution of the characteristic of the plurality of electrograms.

* * * * *